United States Patent [19]

Benzie et al.

[11] 4,230,634

[45] Oct. 28, 1980

[54] MANUFACTURE OF ORGANIC NITRILES

[75] Inventors: Robert J. Benzie; Dhafir Y. Waddan, both of Middlesbrough, England

[73] Assignee: Imperial Chemical Industries Limited, London, England

[21] Appl. No.: 41,258

[22] Filed: May 21, 1979

Related U.S. Application Data

[63] Continuation-in-part of Ser. No. 884,548, Mar. 8, 1978, abandoned.

[30] Foreign Application Priority Data

Mar. 28, 1977 [GB] United Kingdom ............... 12916/77

[51] Int. Cl.$^2$ ............................................. C07C 120/02
[52] U.S. Cl. ............................ 260/465.3; 260/465.8 R
[58] Field of Search ....................................... 260/465.3

[56] References Cited

U.S. PATENT DOCUMENTS

| | | | |
|---|---|---|---|
| 3,849,472 | 11/1974 | Waddan | 260/465.3 |
| 4,096,171 | 6/1978 | Benzie | 260/465.3 |

FOREIGN PATENT DOCUMENTS

| | | | |
|---|---|---|---|
| 1429169 | 3/1976 | United Kingdom | 260/465.3 |
| 1429651 | 3/1976 | United Kingdom | 260/465.3 |

Primary Examiner—Joseph P. Brust
Attorney, Agent, or Firm—Cushman, Darby & Cushman

[57] ABSTRACT

A process for the manufacture of adiponitrile is described by reacting butadiene with hydrogen cyanide and a catalyst which is a complex of a copper salt and an organic nitrile to form 3-pentenenitrile, which is then hydrocyanated to adiponitrile in which the solvent and sole nitrile complexing agent for the copper is 3-methylglutaronitrile or a mixture of 3-methylglutaronitrile with 2-ethylsuccindinitrile or with 2-ethylsuccindinitrile and adiponitrile.

7 Claims, No Drawings

MANUFACTURE OF ORGANIC NITRILES

CROSS-REFERENCE TO RELATED APPLICATIONS

This is a continuation-in-part of our earlier application Ser. No. 884,548 filed Mar. 8, 1978, and now abandoned.

This invention relates to the manufacture of adiponitrile and more particularly to the manufacture of adiponitrile by reaction of olefinic compounds with hydrogen cyanide in the presence of a catalyst. This application is a continuation in part of application Ser. No. 884,548 now abandoned.

In British Pat. No. 1,429,651 there is described and claimed a process for the manufacture of organic nitriles which comprises reacting an olefin with hydrogen cyanide in the presence of a catalytic amount of a complex of a Group IB metal salt e.g. a copper salt and an organic nitrile, the said complex being formed by mixing the said metal salt with the organic nitrile before or at the same time as it is mixed with the olefin and hydrogen cyanide. The process may be used to produce 3-pentenenitrile from butadiene and the latter may be converted to adiponitrile.

We have found that a particularly valuable nitrile for forming the said complex with a copper salt is a dinitrile of the formula $C_4H_8(CN)_2$.

Accordingly a process for the manufacture of adiponitrile comprises:

(i) reacting a mixture of
  (a) butadiene and
  (b) hydrogen cyanide in
  (c) a solvent in the presence of
  (d) as catalyst a complex of a copper salt and an organic nitrile, the catalyst being used in an amount of 0.0005 to 0.1 mole per mole of butadiene, the molar ratio of butadiene to hydrogen cyanide being 2:1 to 1:4, and the catalyst complex being formed by mixing the said copper salt with the said organic nitrile before or at the same time as it is mixed with the butadiene and hydrogen cyanide the temperature being within the range $-25°$ C. to 200° C. to produce 3-pentenenitrile, and (ii) reacting the 3-pentenenitrile produced in (i) with further hydrogen cyanide in the presence of a catalyst to give adiponitrile, in which there is used in (i) as solven and sole nitrile complexing agent a di-nitrile selected from the group consisting of adiponitrile, 3-methylglutaronitrile, a mixture of adiponitrile and 3-methylglutaronitrile, a mixture of adiponitrile and 2-ethylsuccindinitrile, a mixture of 3-methylglutaronitrile and 2-ethylsuccindinitrile and a mixture of adiponitrile, 3-methylglutaronitrile and 2-ethylsuccindinitrile.

The copper salt may be an inorganic acid salt, for example the sulphate or phosphate, but especially the halide. Important halides are the chlorides, bromides and iodides, for example cuprous chloride, cuprous bromide and cuprous iodide. Alternatively an organic acid salt may be used, for example the salt of an aliphatic acid, for example the acetate or lactate.

The complex of the dinitrile with the copper salt is formed by mixing the components. It is important that copper salt is mixed with the said dinitrile before or at the same time as it is mixed with the butadiene and the hydrogen cyanide. Both the butadiene and the hydrogen cyanide will form a complex with the copper and if this occurs before the introduction of the said dinitrile formation of the desired complex with the latter may be precluded.

The said dinitrile used to form the complex with the Group IB metal salt is used in substantially more than the stoichiometric amount required to form a complex with the copper because the said dinitrile is also used as a solvent.

Stage (i) of the process of our invention is carried out from $-25°$ C. to 200° C., preferably from 20° to 150° C., and more preferably from 50° to 120° C. Owing to the volatility and toxicity of hydrogen cyanide the reaction is preferably conducted in a closed vessel under autogeneous pressure, or, if desired, under deliberately raised pressure, for example at a pressure of from 1 to 50 atmospheres. Agitation of the reactants is desirable. The reaction is continued for a time sufficient to give a suitable conversion which will normally be for from a few minutes, for example 5 minutes, up to a period of several days, for example 5 days.

Owing to the high boiling point and relative non-volatility of the said dinitriles a particularly suitable form of process for continuous, semi-continuous or batch operation of stage (i), is to pass the butadiene and hydrogen cyanide into the said dinitrile containing the complex of the copper salt and the said dinitrile and to remove therefrom as a vapour the relatively volatile 3-pentenenitrile. This method has the advantage that the copper salt complex remains in solution in the said dinitrile, so facilitating recycling of the catalyst.

The butadiene and the hydrogen cyanide may be used in equimolar proportions or an excess of either may be used, i.e. within the molar range of butadiene to hydrogen cyanide of 2:1 to 1:4. The complex of the copper salt and the said dinitrile is used in catalytic amount i.e. within the range 0.0005 to 0.1 moles of each per mole of butadiene although we prefer that the proportion of the said complex is from 0.005 to 0.05 moles per mole of butadiene.

The 3-pentenenitrile formed in the process may be separated from the reaction mixture, for example, by first removing any excess butadiene and/or hydrogen cyanide by distillation or by simply venting the apparatus. The 3-pentenenitrile may then be separated from catalyst residues by conventional methods such as filtration with or without extraction with solvent, or by distillation. The process may readily be adapted to continuous operation.

U.S. Pat. No. 2,509,859 describes the reaction of butadiene and hydrogen cyanide in the presence of a copper halide, for example cuprous chloride, to give 3-pentenenitrile. Although the reaction is described as catalytic good yields of 3-pentenenitrile are obtained only if substantially equimolar proportions of butadiene and copper halide are used. With catalytic proportions, for example 0.006 moles of cuprous chloride per mole of butadiene, both the conversion of butadiene and the yield of 3-pentenenitrile are low. Compared with the process of U.S. Patent Specification No. 2,509,859 stage (i) of the process of our invention enables the conversion to be effected in good yield using only a catalytic amount of copper salt (in the form of its complex with the said dinitrile) instead of the equimolar amount required by the prior process.

The 3-pentenenitrile produced in stage (i) of the process of the invention is further reacted with hydrogen cyanide in the process of a catalyst to give adiponitrile.

This reaction is known and is described for example in U.S. Pat. Nos. 3,496,215, 3,496,217, 3,496,218 and 3,846,474. The catalyst used may be a zerovalent nickel compound optionally activated by a promoter. For example, the catalyst may have the general formula Ni (PXYZ)$_4$ wherein X is OR and Y and Z are of the group consisting of R and OR and R is an alkyl or aryl group having up to 18 carbon atoms. If desired any of the R's in a given PXYZ ligand may be joined together. Ligands of this type include the aryl phosphites e.g. triphenyl phosphite, tri-(m- and p-methoxy) phenyl phosphite, tri-m-tolyl phosphite and tri-p-tolyl phosphite. Other zerovalent nickel compounds which may be used include N-bonded nitrile complexes of the formula Ni (PXYZ)$_3$R$^2$CN and olefin bonded complexes of the formula Ni (PXYZ)$_2$A where X, Y and Z are as defined above. Catalysts of these types and suitable promoters are reviewed in U.S. Pat. No. 3,846,474 and suitable reaction conditions are described therein.

The product of stage (ii) of the process of the present invention is adipontrile together with lesser amounts of methylglutaronitrile and ethylsuccinonitrile (see again U.S. Pat. No. 3,846,474). As adiponitrile is the desired product the two other nitriles are unwanted waste and their use therefore in state (i) of the process of the present invention is economically beneficial as well as providing the added technical advantage that any carryover of dinitrile from stage (i) to stage (ii) is immaterial as they are already present. The preferred dinitrile is methylglutaronitrile because this is the major coproduct but in practice methylglutaronitrile together with small amounts of ethylsuccinonitrile and/or adiponitrile will be used as the byproduct dinitriles are most commonly recovered from stage (ii) as a mixture and it is this stage which provides the most convenient source of dinitriles for stage (i) of the process. For example, the dinitrile preferably comprises at least 80% methylglutaronitrile e.g. 92.5% methylglutaronitrile, 5% ethylsuccinonitrile and 2.5% adiponitrile. Clearly, adiponitrile itself may be used in stage (i) of the process but this is economically less advantageous as adiponitrile is the desired product of the process and should not therefore be recirculated.

Adiponitrile may be hydrogenated to hexamethylene diamine, a valuable intermediate for polycondensation with dicarboxylic acids to give polyamides, especially, for example, with adipic acid to give polyhexamethylene adipamide (nylon 6,6) a well-known polyamide for use in the manufacture of mouldings and for melt spinning into synthetic fibres.

It has already been proposed to react butadiene and hydrogen cyanide in the presence of catalytic amounts of certain catalysts, for example certain zerovalent nickel catalysts, as described, for example, in United Kingdom Pat. No. 1,104,140. Such processes give mixtures of linear pentenenitriles, which are convertible by further reaction with hydrogen cyanide into adiponitrile, and branched methylbutene nitriles which cannot be converted directly to adiponitrile. The proportion of linear pentenenitriles compared with branched methylbutene nitriles produced in such processes is not normally in excess of 70% by weight (or molar). It is an advantage of stage (i) of the process of our invention that the proportion of linear 3-pentenenitrile, directly convertible to adiponitrile, which is produced is appreciably higher, at least 80% by weight (or molar) and usually more than 90%. Moreover, the zerovalent nickel catalysts used in the prior process are sensitive to moisture, whereas the catalysts used in stage (i) of our process are not. Thus anhydrous conditions are not required, and it is not, therefore, necessary, for example, to specially dry the butadiene and hydrogen cyanide.

The invention is illustrated but not limited by the following Examples.

EXAMPLE 1

Cuprous bromide (6 g 0.042 mol) was added to a total of 20 ml adiponitrile, warmed (60° C.) until complete solution was attained then cooled to obtain small crystals before charging to a pressure reactor.

After purging with nitrogen, butadiene (100 ml; 62 g; 1.15 g mol), and hydrogen cyanide (50 ml; 34.4 g; 1.27 g mol) were charged to the reactor.

The reactor was heated until the internal temperature reached the required value (see Table below) (in approximately 1 hour) then maintained at this temperature for the required time (see Table below). The low-boiling material was then distilled off from the adiponitrile and cuprous bromide, and the 3-pentenenitrile product in the distillate estimated by gas-liquid chromatography. The percentage conversion of butadiene to 3-pentenenitrile for various times of reaction and at various temperatures is shown in the following Table 1. In addition 6-8% of butadiene is converted to 2-methylbut-3-enenitrile

TABLE 1

| | % Butadiene Converted to 3-Pentenenitrile | | |
|---|---|---|---|
| | Reaction time (hours) | | |
| Temperature °C. | 2 | 5 | 10 |
| 100 | 47 | 40 | 72 |
| 120 | 37 | 53 | 72 |
| 140 | 66,70 | — | 66 |

EXAMPLE 2

The reaction was carried out continuously by passing an equimolar mixture of butadiene and hydrogen cyanide at a rate of 15 g/hr through a liquid catalyst system composed of 10 g cuprous bromide in 50 ml adiponitrile maintained at 160° C. The gaseous effluent was cooled and the liquid product contained 3-pentenenitrile made at a rate of 1.5 g/hr.

EXAMPLE 3

This example was carried out to show the advantage of a dinitrile solvent, namely adipontrile, in the manufacture of 3-pentenenitrile when the catalyst is recycled, compared with the use of 3-pentenenitrile itself as solvent.

The following charge:
cuprous bromide: 6 g
lithium bromide: 1 g
hydrogen cyanide: 37 g
butadiene: 60 g
solvent (see Table 2): 10 g
was placed in an autoclave and heated at 120° C. for 10 hours. The 3-pentenenitrile formed was then distilled off, leaving behind approximately the initial quantity charged when 3-pentenenitrile was used as solvent. The catalyst mixture remaining behind was then used in a repeat experiment with a fresh charge of hydrogen cyanide and butadiene. The conversion of butadiene to 3-pentenenitrile is given in the following Table 2. About 7.5% of the butadiene was converted to 2-methyl-3-butenenitrile in each experiment.

TABLE 2

| Conversion of Butadiene to 3-pentenenitrile (%) | | |
|---|---|---|
| Solvent | Adiponitrile | 3-Pentene-nitrile |
| Initial Reaction | 70.7 | 71.0 |
| First Recycle | 68.6 | 60.0 |
| Second Recycle | 56.2 | 54.3 |

EXAMPLE 4

This example was carried out in a similar way to Example 3 to show the use of methylglutaronitrile, itself obtained from the process claimed, as solvent and sole complexing agent in the manufacture of 3-pentenenitrile. The conversions of butadiene were 77.3% to 3-pentenenitrile and 5.8% to 2-methyl-3-butenenitrile.

EXAMPLE 5

22.73 g of solution containing 21.0 g of dry 3-pentenenitrile produced as described in Examples 1 to 4, 0.48 g of tetra kis (tri(meta/para)tolylphosphite) nickel, 1.16 g of tri(meta/para)tolylphosphite and 0.09 g of anhydrous zinc chloride was added to a 50 ml 3-neck flask fitted with a condenser, stirrer and gas inlet. Hydrogen cyanide was bubbled through the solution maintained at 40° C. at a rate of 2.04 g/hr. After 2¼ hr the hydrogen cyanide feed was stopped and G.C. analysis of the product showed it to contain 57.19% dinitrile of which 83% was the linear adiponitrile, 15% methylglutaronitrile and 2% ethylsuccinonitrile. Separation of the latter two nitriles produced a product consisting largely of methylglutaronitrile which could be used as in Example 4 above.

I claim:

1. In a process for the manufacture of adiponitrile which comprises:
   (i) reacting a mixture of
      (a) butadiene and
      (b) hydrogen cyanide in
      (c) a solvent in the presence of
      (d) as catalyst a complex of a copper salt and an organic nitrile,
   the catalyst being used in an amount of 0.0005 to 0.1 mole per mole of butadiene, the molar ratio of butadiene to hydrogen cyanide being 2:1 to 1:4 and the catalyst complex being formed by mixing the said copper salt with the said organic nitrile before or at the same time as it is mixed with the butadiene and hydrogen cyanide the temperature being within the range −25° C. to 200° C. to produce 3-pentenenitrile, and
   (ii) reacting the 3-pentenenitrile produced in (i) with further hydrogen cyanide in the presence of a catalyst to give adiponitrile,
   the improvement whereby there is used in (i) as solvent and sole nitrile complexing agent a di-nitrile selected from the group consisting of 3-methylglutaronitrile, a mixture of 3-methylglutaronitrile and 2-ethylsuccinidinitrile and a mixture of adiponitrile, 3-methylglutaronitrile and 2-ethylsuccindinitrile.

2. The process of claim 1 in which the copper salt is a phosphate, sulphate, halide or salt of an aliphatic acid.

3. The process of claim 1 in which the copper salt is cuprous chloride or cuprous bromide.

4. The process of claim 1 in which the dinitrile used in stage (i) is a recycled byproduct of stage (ii) of the process.

5. The process of claim 4 in which the dinitrile is a mixture composed of methylglutaronitrile with lesser amounts of adiponitrile and ethylsuccinonitrile.

6. The process of claim 4 in which the dinitrile is a mixture composed of methylglutaronitrile with a lesser amount of ethylsuccinonitrile.

7. In a process for the manufacture of adiponitrile which comprises:
   (i) reacting a mixture of
      (a) butadiene and
      (b) hydrogen cyanide in
      (c) a solvent in the presence of
      (d) as catalyst a complex of a copper salt and an organic nitrile,
   the catalyst being used in an amount of 0.0005 to 0.1 mole per mole of butadiene, the molar ratio of butadiene to hydrogen cyanide being 2:1 to 1:4 and the catalyst complex being formed by mixing the said copper salt with the said organic nitrile before or at the same time as it is mixed with the butadiene and hydrogen cyanide the temperature being within the range −25° C. to 200° C. to produce 3-pentenenitrile, and
   (ii) reacting the 3-pentenenitrile produced in (i) with further hydrogen cyanide in the presence of a catalyst to give adiponitrile,
   the improvement whereby there is used in (i) as solvent and sole nitrile complexing agent a di-nitrile selected from the group consisting of 3-methylglutaronitrile, a mixture of 3-methylglutaronitrile and 2-ethylsuccindinitrile and a mixture of adiponitrile, 3-methylglutaronitrile and 2-ethylsuccindinitrile, and the di-nitrile used in (i) is a recycled by product of step (ii) of the process.

* * * * *